United States Patent [19]

Masuda et al.

[11] 4,076,663
[45] Feb. 28, 1978

[54] WATER ABSORBING STARCH RESINS

[75] Inventors: Fusayoshi Masuda; Kazuo Nishida; Akira Nakamura, all of Kyoto, Japan

[73] Assignee: Sanyo Chemical Industries, Ltd., Kyoto, Japan

[21] Appl. No.: 671,148

[22] Filed: Mar. 29, 1976

[30] Foreign Application Priority Data

Mar. 27, 1975 Japan .................................. 50-37669

[51] Int. Cl.$^2$ .............................................. C08L 3/06
[52] U.S. Cl. ............................ 260/17.4 GC; 128/284; 128/285; 128/290 P; 260/17 R; 260/17.4 R; 260/17.4 CL; 260/17.4 ST
[58] Field of Search .................. 260/17.4 ST, 17.4 R, 260/17 R, 17.4 GC, 17.4 CL; 128/284, 285, 290

[56] References Cited

U.S. PATENT DOCUMENTS

| | | | |
|---|---|---|---|
| 3,505,257 | 4/1970 | Conte et al. | 260/17.4 |
| 3,628,534 | 12/1971 | Donohue | 128/285 |
| 3,670,731 | 6/1972 | Harmon | 128/284 |
| 3,889,678 | 6/1975 | Chatterjee | 260/17.4 |
| 3,995,998 | 12/1976 | Rowland et al. | 260/17.4 |

Primary Examiner—Edward M. Woodberry
Attorney, Agent, or Firm—Oblon, Fisher, Spivak, McClelland & Maier

[57] ABSTRACT

A highly water-absorbent resin is produced by polymerizing (A) starch or cellulose, (B) at least one monomer having a polymerizable double bond which is water-soluble or becomes water-soluble by hydrolysis and (C) a crosslinking agent, and subjecting, if necessary, the resulting product to hydrolysis.

21 Claims, No Drawings

WATER ABSORBING STARCH RESINS

BACKGROUND OF THE INVENTION

1. Field of the Invention

The present invention relates to a water-absorbent resin. It relates, more particularly, to a starch-or cellulose-based water-absorbent resin.

2. Descritpion of the Prior Art

Heretofore, non-woven fabrics, papers, pulps, spongy urethane resins, natural sponges, and the like have been used as water-absorbing materials for sanitary napkins, diapers, disposable dustcloths for kitchens, etc. However, these materials have low-water-absorbences and have not been sufficiently satisfactory for the above-mentioned purposes. In recent years, substitutes for these materials, such as cross-linked polyethylene oxide, cross-linked polyvinylalcohol and hydrolyzed products of starch-polyacrylonitrile-grafted polymer have appeared on the market. These products, however, still suffer from significant disadvantages in that their water-absorbences, though relatively high are still not sufficiently satisfactory in that they are expensive because of inherent difficulties in their production processes; in that some create problems of disposal because they are not biologically decomposable, etc. Consequently, there still exists a need for a highly water absorbent resin which is suitable for commercial production.

SUMMARY OF THE INVENTION

Accordingly, it is one object of this invention to provide a process for easily producing resins having high water-absorbences.

It is another object of this invention to provide resins having high water-absorbences which are biodegradable.

Briefly, these and other objects of the invention as hereinafter will become more readily apparent have been attained broadly by providing a process which comprises polymerizing (A) at least one polysaccharide selected from the class consisting of starches and cellulose, (B) at least one monomer having a polymerizable double bond which is water-soluble or becomes water-soluble by hydrolysis, and (C) a cross-linking agent, and subjecting, if necessary the resulting product to hydrolysis.

The starch to be used in the present invention is not particularly critical. Suitable ones include for example natural starches such as sweet potato starch, potato starch, wheat starch, corn starch, rice starch, tapioca starch, and the like, and processed or modified starches such as α-starch, dextrine, oxidized starch, dialdehyde starch, alkyl-etherified starch, allyl-etherified starch, oxyalkylated starch, aminoethyl-etherified starch, cyanoethyl-etherified starch and the like.

Simiarly, the cellulose to be used in the present invention is not particularly critical. Suitable ones include for example celluloses obtained from wood, leaves, stems, bast, seed fluffs, and the like; and modified celluloses such as alkyl-etherified cellulose, organic-acid-esterified cellulose, oxidized cellulose, hydrocellulose, and the like. Among these polysaccharides, natural starches such as wheat starch and corn starch, and α-starches thereof, are preferred.

Suitable water-soluble monomers to be used in the present invention include monoethylenically unsaturated compounds (or compounds having a polymerizable double bond), having at least one hydrophilic radical, such as carboxyl, carboxylic acid anhydride, carboxylic acid salt, sulfonic acid, sulfonic acid salt, hydroxyl, ether, amide, amino and quaternary ammonium salt groups. Examples of suitable water-soluble monomers are as follows:

1. Carboxyl group-containing monomers: monoethylenically unsaturated mono or poly-carboxylic acids, such as (meth) acrylic acid (meaning acrylic acid or methacrylic acid. Similar notations are used hereinafter), maleic acid and fumaric acid;

2. Carboxylic acid anhydride group-containing monomers: monoethylenically unsaturated polycarboxylic acid anhydrides (such as maleic anhydride);

3. Carboxylic acid salt-containing monomers: water-soluble salts (alkali metal salts, ammonium salts, amine salts, etc.) of monoethylenically unsaturated mono- or poly- carboxylic acids [such as sodium (meth)acrylate, trimethylamine (meth)acrylate, triethanolamine (meth) acrylate, sodium maleate, methylamine maleate];

4. Sulfonic acid group-containing monomers: aliphatic or aromatic vinyl sulfonic acids (such as vinylsulfonic acid, allyl sulfonic acid, vinyltoluenesulfonic acid, styrene sulfonic acid), (meth)acrylic sulfonic acids [such as sulfopropyl (meth) acrylate, 2-hydroxy-3-(meth)acryloxy propyl sulfonic acid];

5. Sulfonic acid salt group-containing monomers: alkali metal salts, ammonium salts, amine salts of sulfonic acid group-containing monomers as mentioned above.

6. Hydroxyl group-containing monomers: monoethylenically unsaturated alcohols [such as (meth)allyl alcohol], monoethylenically unsaturated ethers or esters of polyols (alkylene glycols, glycerol, polyoxyalkylene polyols), such as hydroxethyl (meth)acrylate, hydroxypropyl (meth)acrylate, triethylene glycol (meth)acrylate, poly(oxyethylene oxypropylene) glycol mono (meth)allyl ether (in which hydroxyl groups may be etherified or esterified).

7. Amide group-containing monomers: (meth) acrylamide, N-alkyl (meth)acrylamides (such as N-methylacrylamide, N-hexylacrylamide), N,N-dialkyl (meth)acryl amides (such as N,N-dimethylacrylamide, N,N'-di-n-propylacrylamide), N-hydroxyalkyl (meth)acrylamides [such as N-methylol(meth)acrylamide, N-hydroxyethyl (meth)acrylamide], N,N-dihydroxyalkyl (meth)acrylamides [such as N,N-dihydroxyethyl (meth)acrylamide], vinyl lactams (such as N-vinylpyrrolidone);

8. Amino group-containing monomers: amino group-containing esters (e.g. dialkylaminoalkyl esters, dihydroxyalkylaminoalkyl esters, morpholinoalkyl esters, etc.) of monoethylenically unsaturated mono- or di-carboxylic acid [such as dimethlaminoethyl (meth)acrylate, diethylaminoethyl (meth)acrylate, morpholinoethyl (meth)acrylate, dimethyl aminoethyl fumarate], heterocyclic vinyl compounds [such as vinyl pyridines (e.g. 2-vinyl pyridine, 4-vinyl pyridine, N-vinyl pyridine), N-vinyl imidazol]; and 9. Quaternary ammonium salt group-containing monomers: N,N,N-trialkyl-N-(meth)acryloyloxyalkylammonium salts [such as N,N,N-trimethyl-N-(meth)acryloyloxyethylammonium chloride, N,N,N-triethyl-N-(meth)acryloyloxyethylammonium chloride, 2-hydroxy-3-(meth)-acryloyloxypropyl trimethyl ammonium chloride], and monomers as mentioned in British patent specification No. 1,034,296.

Suitable monomers which become water-soluble by hydrolysis, for use in this invention instead of or in conjunction with the water-soluble monomers, include monethylenically unsaturated compounds having at least one hydrolyzable group, such as ester and nitrile groups. Such monomers having an ester group include for example, lower alkyl ($C_1$–$C_3$) esters of monoethylenically unsaturated carboxylic acids, such as methyl (meth)acrylate, ethyl (meth)acrylate and 2-ethylhexyl (meth)acrylate; and esters of monoethylenically unsaturated alcohols [vinyl esters, (meth)-allyl ester, etc.], such as vinyl acetate and (meth) allyl acetate. Suitable nitrile group-containing monomers include (meth) acrylonitrile.

Among these monomers having a polymerizable double bond which are water-soluble or become water-soluble by hydrolysis, water-soluble monomers which do not need hydrolysis after polymerization are preferred from the viewpoint of providing an easy process for producing water-absorbing resins. Further, from the viewpoint of providing water-absorbing resins having a high water-absorbence, the preferred water-soluble monomers are carboxyl group-containing monomers such as (meth)-acrylic acid and maleic acid anhydride; carboxylic acid salt group-containing monomers such as sodium (meth)acrylate, trimethylamine (meth)acrylate and triethanolamine (meth)acrylate, and quaternary ammonium salt group-containing monomers such as N,N,N-trimethyl-N-(meth)acryloyloxyethylammonium chloride. In order to obtain water-absorbing resins having a high water-absorbence, it is more preferred to use the above-mentioned carboxyl group-containing monomers and then to neutralize, with an alkali, the resulting polymers after polymerization.

Suitable cross-linking agents (C) for use in the present invention include any that can provide cross-linked reaction products together with the polysaccharide (A), and the monomer (B). Such cross-linking agents include, for example, (1) compounds having at least two polymerizable double bonds; (2) compounds having at least one polymerizable double bond and at least one functional group reactive with the monomer (B); (3) compounds having at least two functional groups reactive with the monomer (B); and (4) polyvalent metal compounds which can form ionic crosslinkages.

Suitable compounds (1) having at least two polymerizable double bonds include: (i) di- or polyvinyl compounds (such as divinyl benzene, divinyl toluene, divinyl xylene, di-vinyl ether, divinyl ketone and trivinyl benzene); (ii) di-or poly-esters of unsaturated mono- or poly-carboxylic acids with polyols such as di- or tri-(meth)acrylic acid esters of polyols (such as ethylene glycol, trimethylol propane, glycerine, polyoxyethylene glycols, polyoxypropylene glycols, and the like; unsaturated polyesters [that can be obtained by reacting any of the above-mentioned polyols with an unsaturated acid such as maleic acid); and di- or tri-(meth) acrylic acid esters that can be obtained by reacting polyepoxide with (meth)acrylic acid]; (iii) bis(meth)acrylamides such as N,N-methylene-bisacrylamide; (iv) carbamyl esters that can be obtained by reacting polyisocyanates (such as tolylene diisocyanate, hexamethylene diisocyanate, 4,4'-diphenyl methane diisocyanate, and the like and NCO-containing prepolymers obtained by reacting such diisocyanates with active hydrogen atom-containing compounds) with hydroxyl group-containing monomers, such as di-(meth)acrylic acid carbamyl esters obtainable by reacting the above mentioned diisocyanates with hydroxyethyl (meth)acrylate; (v) di- or poly-(meth) allyl ethers of polyols (such as alkylene glycols, glycerol, polyalkylene glycols, polyoxyalkylene polyols, carbohydrates, and the like, such as polyethylene glycol diallyl ether, allylated starch, and allylated cellulose; (vi) di- or poly-allyl esters of polycarboxylic acids, such as diallyl phthalate, diallyl adipate, and the like; and (vii) esters of unsaturated mono- or poly-carboxylic acids with mono(meth)-allyl esters of polyols, such as (meth) acrylic acid ester of polyethylene glycol monoallyl ether.

Suitable compounds (2) having at least one polymerizable double bond and at least one functional group reactive with the monomer (B) include ethylenically unsaturated compounds containing at least one group reactive with carboxyl, carboxylic acid anhydride, hydroxyl, amino or amide groups. Such compounds include N-methylol (meth)acrylamide, glycidyl (meth)acrylate, and the like.

Suitable compounds (3) having at least two functional groups reactive with the monomer (B) include di- or poly-functional compounds which contain groups reactive with carboxyl, carboxylic acid anhydride, hydroxyl, amino or amide groups. Examples are glyoxal; polycarboxylic acids, such as phthalic acid, adipic acid; polyols, such as ethylene glycol; polyamines, such as alkylene diamines (e.g. ethylene diamine), polyalkylene polyamines, and the like.

Suitable polyvalent metal compounds (4) which can form ionic cross-linkages include oxides, hydroxides and weak acid salts (e.g. carbonate, acetate, and the like of alkaline earth metals (e.g. calcium, magnesium) and zinc, such as calcium oxide and zinc diacetate. These polyvalent metal compounds can be used in combination with the monomer (B) containing carboxyl or sulfonic groups.

Among these cross-linking agents (C), the preferred forms are a diester of (meth)acrylic acid with an alkylene ($C_2$–$C_6$) glycol, polyoxyalkylene-($C_2$–$C_4$) glycol having a molecular weight of less than 400, bis(meth)acrylamide, and oxides of alkaline earth metals and zinc. The cross-linking agent used in the present invention remarkably improves the water-absorbence as compared with that of a polymer which is not cross-linked.

The proportion of the ingredients (A), (B) and (C) used in the present invention is not critical and can vary widely within the scope of the present invention, i.e., in a range such that the resulting polymer has high water-absorbence and water insolubility. The weight ratio of (A) : (B) : (C) usually is 100 : 10–3,000 : 0.0001–20, preferably is 100 : 50–1,000 : 0.001–10, and more preferably is 100 : 100–500 : 0.01–5. In addition to the essential components (A), (B) and (C), there may be used in the present invention one or more other comonomers such as styrene, ethylene, propylene, butene, methyl(meth)acrylate and the like.

The raw materials (A), (B) and (C) may be reacted by various methods. The polymerization reaction can, for example, be carried out by subjecting a mixture of (A), (B) and (C) to polymerization conditions; by adding cross-linking agent (C) to the reaction product of (A) and (B); or by adding (C) to the reaction mixture of (A) and (B) during reaction. When the raw material (A) is a starch (except for α-starch), it is preferred to change the starch, beforehand into α-type by, for example, heating it in a solvent such as water, alcohol, or a mixture therof. Suitable temperature for the change into α-type is not critical and may vary within a wide range, depending upon the kind of starch and the heating period used. It is generally 40°–100° C.

The polymerization reaction may be performed under various conditions such as with irradiation of radioactive, electronic or ultraviolet rays, etc., or in the presence of a radical polymerization catalyst such as ceric salt-type redox catalyst, hydrogen peroxide or hydrogen peroxide-type redox catalyst, benzoyl peroxide, azobisisobutyronitrile, azobisisovaleric acid, ammonium persulfate or sodium persulfate or persulfate-type redox catalyst, and the like. Among these polymerization processes, it is preferred to employ the polymerization process using the ceric salt-type catalyst or hydrogen peroxide-type catalyst, from the viewpoints of increasing the graft-polymerization ratio between (A) and (B) and providing a water-absorbing resin having a high water-absorbence which is one of the objects of the present invention.

In the polymerization of the present invention, a solvent, such as water, methanol, ethanol, acetone, N,N-dimethylformamide, dimethyl sulfoxide or a mixture thereof may be used, if necessary. The polymerization temperature to be used when a catalyst is employed in the present invention depends on the type of catalyst, but is usually from 10° to 150° C, preferably 20° to 100° C.

When a monomer which becomes water-soluble by hydrolysis is used as all or a part of the monomer (B) in the present invention, the hydrolyzable groups of the monomers are hydrolyzed partially or completely after the polymerization of (A), (B) and (C). The hydrolysis may be carried out by an conventional known method. Generally, however, the hydrolysis is carried out in an aqueous solvent or in a mixed solvent of water and alcohol, using a catalyst such as sodium hydroxide or potassium hydroxide, and the like, at a temperature between 10° and 150° C. When free carboxyl or sulfonic acid groups, and the like, are present in the resulting resin, such acid groups may be neutralized by any conventional known method to form a salt (such as an alkali-metal salt, an ammonium salt, an amine salt, and the like).

The reaction product obtained by the process of the present invention may then be dried and pulverized to form an end product, or if necessary, may be washed with a mixed solvent or water and alcohol, and then dried and pulverized to form an end product. Also, the reaction may be diluted with water, or after drying and pulverization, may be dispersed in water to form an end product (dispersion).

The water-absorbing resins obtained by the process of the present invention may contain or be mixed with fillers, fibrous materials (such as pulp, cotton, etc.), pigments, ultraviolet ray absorbing agents, antioxidants, agricultrual chemicals (such as antifungal agents, bactericides, insecticides, herbicides or fertilizers), perfumes, deodorants and the like.

Appropriate applications of the water-absorbing resins obtained according to the present invention extend over a wide variety of fields. For example, when the resins are used for absorbent dressings for absorbing body fluids (such as paper diapers, sanitary napkins, gauze, paper towels, etc.), products having an excellent liquid-absorbence can be obtained. When mixed with soil, they elevate its water retention characteristics. When used for building materials for interior portions or interior finishes, they provide products having dew-condensation preventing properties. Agricultural chemicals, fertilizers, perfumes, and the like will maintain their effects for a longer time when the resins are impregnated with them.

The water-absorbing resins obtained according to the present invention may be applied by any known methods. Such methods include the method wherein the resin is mixed in the form of a powder with pulp, soil, plastics, or the like; the method wherein the resin is sprayed in the form of an aqueous dispersion onto a substrate such as pulp, cloth, paper, wood, stone, concrete or the like; the method wherein a substrate such as pulp, cloth, paper, wood, stone, concrete or the like is immersed into an aqueous dispersion of a powder of the resin or an aqueous solution of the resin and then the substrate is dried; and the method wherein such a substrate is immersed into such an aqueous dispersion or solution and the mixture is kneaded, followed by drying. There is also a method which may be employed, wherein after (A), (B) and (C) are mixed with pulp, cotton, agricultural chemicals, perfumes or soil, they are subjected to polymerization, or thereafter, if necessary, to hydrolysis, and then dried for use of the resulting product as an end product.

The water-absorbing resin compositions obtained in the present invention have various advantages: they possess an excellent absorbence for salt solution, urine, blood, etc. in addition to water [the water-absorbence is usually at least 60 ml/g, preferably 100~500ml/g, more preferably 150~500 ml/g (active component)]; they can be stored for long periods in the atmosphere since their ability for absorbing moisture in air is extremely low when dry, in spite of their excellent water-absorbing ability; they are relatively inexpensive because they can be produced easily; since starch and/or cellulose is used as a portion of the indispensable components, they have excellent biodegradable properties making their disposal easy; and even when starch is used as a part of the indispensable components, the water-absorbing resins obtained in the present invention are resistant to enzymes such as amylase. In addition, the fact that they have biodegradable properties and show resistance to enzymes particularly makes them most suitable for use as paper diapers, sanitary napkins, and the like.

Having generally described the invention, a more complete understanding can be obtained by reference to certain specific examples, which are included for purposes of illustration only and are not intended to be limiting unless otherwise specified. Parts in the examples are by weight.

EXAMPLE 1

Seventy parts of corn starch, 200 parts of water and 1,200 parts of methanol were put into a reaction vessel equipped with a stirrer, a nitrogen inlet tube and a thermometer. The resulting mixture was stirred for an hour under an atmosphere of nitrogen at 55° C and then cooled to 30° C. To the mixture were added 120 parts of acrylamide, 50 parts of a solution of ammonium ceric nitrate (1/10 mol cerium ions in 1 N nitric acid), and 0.1 part of methylenebisacrylamide, and then the reaction mixture was subjected to polymerization while stirring at 35° C for 3 hours to obtain a somewhat viscous white suspension. A powdery product was separated from the suspension by filtration, and was washed with a water-methanol mixture (the ratio of water to methanol = 2 : 10 by weight) and dried under reduced pressure at 60° C for 3 hours. After pulverization, 176 parts of a powdered product was obtained.

EXAMPLE 2

Thirty parts of wheat starch, 200 parts of water and 600 parts of ethanol were put into a reaction vessel as in Example 1. The mixture was stirred for 1.5 hours under a nitrogen stream at 60° C, and then cooled to 30° C. After the addition of 100 parts of hydroxyethyl methacrylate, 50 parts of a solution of ammonium ceric nitrate (1/10 mol cerium ions in 1 N nitric acid) and 0.1 part of methylenebisacrylamide, the reaction mixture was subjected to polymerization at 45° C for 3 hours while stirring to obtain a suspension of pale-yellow fine particles. Thereafter, the pale-yellow fine particles obtained by filtering the suspension were washed with a water-methanol mixture (water : methanol = 2 : 10 by weight) and dried at 60° C for 5 hours under reduced pressure. After pulverization, 78 parts of a powdered product was obtained.

EXAMPLE 3

Fifty parts of corn starch, 200 parts of water and 1,000 parts of methanol were placed into a reaction vessel as in Example 1. The mixture was stirred for an hour under an atmosphere of nitrogen at 50° C and then it was cooled to 30° C. After the addition of 20 parts of acrylic acid 80 parts of sodium acrylate, 1 part of N,N-methylenebisacrylamide and 0.5 parts of azobisvaleric acid (as a polymerization catalyst), the reaction mixture was subjected to polymerization while stirring at 60° C for 6 hours. The resulting white suspension was treated as in Example 1 to obtain 49 parts of a powdered product.

EXAMPLE 4

Fifty parts of corn starch, 200 parts of water and 1000 parts of methanol were placed into a reaction vessel as in Example 1. The mixture was stirred for an hour under an atmosphere of nitrogen at 55° C and then cooled to 30° C. After the addition of 20 parts of acrylic acid, 80 parts of sodium acrylate, 40 parts of a solution of ammonium ceric nitrate (1/10 mol cerium ion in 1 N nitric acid) and one part of N,N-methylenebisacrylamide, the reaction mixture was subjected to polymerization while stirring at 40° C for 3 hours. The resulting suspension was treated as in Example 1 to obtain 138 parts of a powdered product.

EXAMPLE 5

Fifty parts of fluff pulp (cellulose), 300 parts of water and 900 parts of methanol were placed into a reaction vessel as in Example 1. The mixture was stirred for an hour at 55° C under an atmosphere of a nitrogen and then cooled to 30° C. After the addition of 30 parts of acrylic acid, 70 parts of sodium acrylate, 40 parts of a solution of ammonium ceric nitrate (1/10 mol cerium ions in 1 N nitric acid) and 0.5 part of N,N-methylenebisacrylamide, the reaction mixture was subjected to polymerization while stirring at 45° C for 3 hours to form a white suspension which was treated as in Example 1 to obtain 135 parts of a powdered product.

EXAMPLE 6

Seventy parts of fluff pulp, 300 parts of water and 900 parts of methanol were placed into a reaction vessel as in Example 1. The mixture was stirred for an hour under an atmosphere of nitrogen, and then cooled to 30° C. After the addition of 86 parts of methyl acrylate, 0.5 parts of azobisvaleric acid (as a polymerization catalyst), and 0.5 parts of trixyethylene glycol dimethacrylic acid ester, the reaction mixture was subjected to polymerization while stirring at 65° C for 3 hours to form a white suspension. Thereafter, a solution of 40 parts of sodium hydroxide in 100 parts of water was added to the suspension to carry out hydrolysis at 90° C for 3 hours. The powder obtained by filtering this hydrolyzed suspension was dried under reduced pressure at 60° C for 3 hours. After pulverization, 170 parts of a powdered product was obtained.

EXAMPLE 7

Twenty parts of potato starch and 400 parts of water were placed into a reaction vessel as in Example 1. The mixture was stirred for an hour under an atomosphere of nitrogen at 80° C to change it to α-starch and it was then cooled to 30° C. After the addition of 800 parts of methanol, 40 parts of acrylamide, 40 parts of ethyl acrylate, 0.2 part of 30% $H_2O_2$ solution, 0.1 part of L-ascorbic acid and 0.5 parts of ethylene-glycoldimethacrylate, the reaction mixture was subjected to polymerization while stirring at 35° C for 3 hours to form a white suspension which was treated as in Example 1 to obtain 87 parts of a powdered product.

EXAMPLE 8

Fifty parts of corn starch, 300 parts of water and 1000 parts of methanol were placed into a reaction vessel as in Example 1. The mixture was stirred for an hour under an atmosphere of nitrogen at 50° C and then cooled to 30° C. After the addition of 60 parts of N,N,N-trimethyl-N-acryloyloxyethylammonium chloride, 0.2 parts of N,N-methylenebisacrylamine and 0.2 parts of an 30% aqueous solution of hydrogen peroxide (as a polymerization catalyst) and 0.1 part of L-ascorbic acid, the reaction mixture was subjected to polymerization at 45° C for 3 hours to form a white suspension which was then treated as in Example 1 to obtain 103 parts of a powdered product.

EXAMPLE 9

One hundred and thirty seven parts of corn starch and 600 parts of water were placed into a reaction vessel as in Example 1. The mixture was stirred under an atmosphere of nitrogen at 55° C for 30 minutes and then cooled to 30° C. After the addition of 140 parts of acrylic acid, 60 parts of acrylamide, one part of ethylene glycol dimethacrylic acid ester, and 0.2 part of a 30% aqueous solution of hydrogen peroxide and 0.1 part of L-ascorbic acid, the reaction mixture was subjected to polymerization at 35° C for 3 hours while stirring to form an elastic white solid. After drying at 60° C for 5 hours under reduced pressure, the solid was pulverized to obtain 312 parts of white powder. One hundred parts of this white powder was put into a beaker and 400 parts of a 5% solution of sodium hydroxide in water-methanol mixed solvent (water : methanol = 2 : 8 by weight) was added. After standing at about 20° C for an hour, the resulting mixture was dried at 60° C for 3 hours under reduced pressure and pulverized to obtain 118 parts of white powder.

EXAMPLE 10

One hundred and thirty seven parts of rice starch and 600 parts of water were placed into a reaction vessel as in Example 1. The mixture was stirred at 55° C for 3 hours and then cooled to 30° C. After the addition of 200 parts of acrylic acid, one part of calcium oxide, and 0.2 part of 30% aqueous hydrogen peroxide and 0.1 part of L-ascorbic acid, the reaction mixture was subjected to polymerization while stirring at 35° C for 3 hours to obtain an elastic white solid. Two hundred parts of a 30% aqueous solution of sodium hydroxide was added to this white solid. After the mixture was allowed to stand overnight at 25° C, it was treated as in Example 9 to obtain 361 parts of white powder.

EXAMPLE 11

Thirty parts of fluff pulp was immersed for 5 minutes into 100 parts of the white suspension (1) obtained in Example 3. After the pulp was taken up, it was dried under reduced pressure at 60° C for 3 hours to obtain 40 parts of an impregnated product.

EXAMPLE 12

Eighty five parts of corn starch, and 800 parts of water were put into a reaction vessel as in Example 1. The mixture was stirred for an hour under an atmosphere of nitrogen at 80° C to change it to α-starch, and then cooled to 30° C. After the addition of 120 parts of acrylic acid, 1 part of trioxyethyleneglycol dimethacrylate, 0.2 part of a 30% hydrogen peroxide solution and 0.1 part of L-ascorbic acid, the reaction mixture was subjected to polymerization while stirring at 40° C for 3 hours to form elastic particles. After cooling, 120 parts of a 30% sodium hydroxide solution was added to the particles, which were then allowed to stand overnight at 30° C. After drying, at 60° C for 5 hours under reduced pressure, the particles were pulverized to obtain 227 parts of white powder.

COMPARATIVE EXAMPLE

Examples 4, 9 and 10 were repeated without addition of cross-linking agents to obtain, respectively, water-absorbing resins A, B and C for comparison.

EXAMPLE 13

(Test for absorbency)

The absorbences for water, saline solution and urine, of each product obtained in Examples 1 to 12 and the comparative example were measured. The measuring method comprised putting one gram of each product obtained in Examples 1 to 12 and the comparative example into a beaker; adding 500 ml of each liquid to be absorbed to prepare a dispersion of each product; pouring the dispersion onto a 100 mesh sieve; and measuring the volume of the liquid which flowed through the sieve. Five hundred milliliters minus this volume is defined as the amount of liquid absorbed. Further, for comparison, the liquid absorbence of fluff pulp is also provided. The results are shown in the following table, the liquid absorbence of the water-absorbing resins obtained in the present invention is very excellent.

TABLE

| | | LIQUID ABSORBENCE | | | |
| | | liquid absorbence (ml/g) | | | |
| No. | Sample tested | liquid absorbed water | 0.5 NaCl | 0.1N NaOH | Urine |
| --- | --- | --- | --- | --- | --- |
| 1 | Product obtained In Example 1 | 113 | 40 | 29 | 27 |
| 2 | Product obtained in Example 2 | 81 | 34 | 28 | 30 |
| 3 | Product obtained in Example 3 | 110 | 42 | 32 | 31 |
| 4 | Product obtained in Example 4 | 219 | 58 | 49 | 62 |
| 5 | Product obtained in Example 5 | 192 | 61 | 55 | 60 |
| 6 | Product obtained in Example 6 | 72 | 31 | 32 | 29 |
| 7 | Product obtained in Example 7 | 174 | 32 | 31 | 26 |
| 8 | Product obtained in Example 8 | 215 | 63 | 59 | 60 |
| 9 | Product obtained in Example 9 | 198 | 59 | 55 | 58 |
| 10 | Product obtained in Example 10 | 351 | 82 | 76 | 80 |
| 11 | Product obtained in Example 11 | 64 (110) | 32 (42) | 28 (32) | 27 (31) |
| 12 | Product obtained in Example 12 | 482 | 91 | 86 | 87 |
| A | Water-absorbing resin A | 35 | 5 | 4 | 7 |
| B | Water-absorbing resin B | 41 | 7 | 7 | 8 |
| C | Water-absorbing resin C | 53 | 8 | 9 | 9 |
| D | Fluff pulp | 20 | 11 | 10 | 7 |

Note: The data in parenthesis are based on the amount of active component.

Having now fully described the invention, it will be apparent to one of ordinary skill in the art that many changes and modifications can be made thereto without departing from the spirit or scope of the invention as set forth herein.

What is claimed as new and intended to be secured as Letters Patent is:

1. A process for producing a water-absorbing resin which comprises polymerizing (a) at least one of natural starch and α starch, (b) at least one monomer having a single polymerizable double bond which is a water-soluble or becomes water-soluble by hydrolysis, and (c) a crosslinking agent, and if the monomer (b) is one which becomes water soluble by hydrolysis, thereafter subjecting the resulting product to hydrolysis.

2. The water-absorbing resin having a water-absorbence of at least 60 ml/g obtained by the process of claim 1.

3. The water-absorbing resin having a water-absorbence of from 100 to 500 ml/g obtained by the process of claim 1.

4. The process of claim 1, wherein the crosslinking agent (C) is selected from the group consisting of (1) a compound having at least two isolated polymerizable double bonds, (2) a compound having at least one polymerizable double bond and at least one functional group reactive with the monomer (B), (3) a compound having at least two functional groups reactive with the monomer (B), (4) a polyvalent metal compound which can form ionic crosslinkages and mixtures thereof.

5. The process of claim 4, wherein the compound having at least two isolated polymerizable double bonds is a di- or poly-ester of an unsaturated mono- or polycarboxylic acid with a polyol.

6. The process of claim 4, wherein the compound having at least two polymerizable double bonds is a diester of (meth)acrylic acid with an alkylene($C_2$–$C_6$) glycol or polyoxyalkylene($C_2$–$C_4$)glycol having a molecular weight of less than 400.

7. The process of claim 4, wherein the compound having at least two polymerizable double bonds is a bis-(meth)acrylamide.

8. The process of claim 7, wherein the bis(meth)acrylamide is an N,N-alkylene($C_1$–$C_6$)bis(meth)acrylamide.

9. The process of claim 4, wherein the polyvalent metal compound is an oxide, hydroxide or weak acid salt of a polyvalent metal.

10. The process of claim 9, wherein the polyvalent metal is an alkaline earth metal or zinc.

11. The process of claim 1, wherein the monomer (B) which is water-soluble is a monoethylenically unsaturated compound having at least one hydrophilic group selected from the group consisting of carboxyl, carboxylic acid anhydride, carboxylic acid salt, sulfonic acid, sulfonic acid salt, hydroxyl, ether, amide, amino and quaternary ammonium salt groups.

12. The process of claim 11, wherein the monoethylenically unsaturated compound is a monoethylenically unsaturated carboxylic acid, anhydride thereof or salt thereof.

13. The process of claim 12, wherein the monoethylenically unsaturated compound is (meth)acrylic acid, maleic acid, fumaric acid, a water-soluble salt of said acids or maleic anhydride.

14. The process of claim 11, wherein the monoethylenically unsaturated compound having an amide group is (meth)acrylamide or vinyl lactam.

15. The process of claim 11, wherein the monoethylenically unsaturated compound having a quaternary ammonium salt group is a quaternary (meth)acrylic ester, a quaternary (meth)acrylic amide or a quaternary vinyl compound.

16. The process of claim 1, wherein the monomer (B) which becomes water-soluble by hydrolysis is a monoethylenically unsaturated compound having at least one hydrolyzable group selected from the group consisting of ester and nitrile groups.

17. The process of claim 16 wherein the monomer (B) is (meth)arylonitrile, alkyl ($C_1$-$C_3$) (meth)acrylate or alkyl ($C_1$-$C_3$)vinyl ester.

18. The process of claim 1, wherein the weight ratio of (A) : (B) : (C) is 100 : 10–3,000 : 0.0001–20.

19. The process of claim 1, wherein the weight ratio of (A) : (B) : (C) is 100 : 50–1,000 : 0.001–10.

20. The process of claim 1, wherein the starch is changed into α-type starch in a solvent at an elevated temperature before being used in the polymerization.

21. The process of claim 1, wherein the monomer (B) is a monomer having at least one free carboxyl, carboxylic acid anhydride or free sulfonic group, and said group is neutralized to form a salt after the polymerization.

* * * * *